(12) United States Patent
Despa et al.

(10) Patent No.: US 9,775,957 B2
(45) Date of Patent: Oct. 3, 2017

(54) SMART MODULE FOR INJECTION DEVICES

(71) Applicant: Becton, Dickinson and Company, Franklin Lakes, NJ (US)

(72) Inventors: Mircea Stefan Despa, Cary, NC (US); Michael Yarger, Chapel Hill, NC (US); Adam Martin, Holly Springs, NC (US); Andrew Richards, Durham, NC (US); Sundeep Kankanala, Chapel Hill, NC (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 14/996,155

(22) Filed: Jan. 14, 2016

(65) Prior Publication Data

US 2016/0243318 A1 Aug. 25, 2016

Related U.S. Application Data

(60) Provisional application No. 62/104,593, filed on Jan. 16, 2015, provisional application No. 62/248,984, filed on Oct. 30, 2015.

(51) Int. Cl.
*G08B 19/00* (2006.01)
*A61M 5/50* (2006.01)
(Continued)

(52) U.S. Cl.
CPC ...... *A61M 5/5086* (2013.01); *A61M 5/14244* (2013.01); *A61M 5/20* (2013.01);
(Continued)

(58) Field of Classification Search
CPC .............. G08B 21/18; A61M 2205/18; A61M 2205/3306; A61M 2205/3331;
(Continued)

(56) References Cited

U.S. PATENT DOCUMENTS

2007/0175828 A1* 8/2007 Goedje ................. A61B 5/028 210/646
2009/0043253 A1* 2/2009 Podaima ............... G06F 19/322 604/67

(Continued)

FOREIGN PATENT DOCUMENTS

WO WO 2013/160152 A1 10/2013
WO WO 2014/152704 A1 9/2014

OTHER PUBLICATIONS

Becton, Dickinson & Co., Stella Project IP Assessment & Strategy, Apr. 11, 2016, 24 pages.

*Primary Examiner* — Ojiako Nwugo
(74) *Attorney, Agent, or Firm* — Knobbe Martens Olson & Bear, LLP

(57) ABSTRACT

Described herein is a smart module configured to work with injection devices. The smart module may include electronics such as sensors and indicators, and be programmed to detect environmental parameters. If the sensors detect that a parameter is outside of a predetermined boundary or range, then the indicators may be activated to notify the user that the injection device may not be safe for administering medicine.

22 Claims, 14 Drawing Sheets

(51) Int. Cl.
*A61M 5/20* (2006.01)
*A61M 5/142* (2006.01)
*G08B 21/18* (2006.01)

(52) U.S. Cl.
CPC ............ *A61M 5/50* (2013.01); *G08B 21/18* (2013.01); *A61M 2205/18* (2013.01); *A61M 2205/3306* (2013.01); *A61M 2205/3331* (2013.01); *A61M 2205/3368* (2013.01); *A61M 2205/50* (2013.01); *A61M 2205/581* (2013.01); *A61M 2205/582* (2013.01); *A61M 2205/583* (2013.01)

(58) Field of Classification Search
CPC ...... A61M 2205/3368; A61M 2205/50; A61M 2205/581; A61M 2205/582; A61M 2205/583; A61M 5/14244; A61M 5/20; A61M 5/50; A61M 5/5086
USPC .......................................... 340/521; 600/587
See application file for complete search history.

(56) References Cited

U.S. PATENT DOCUMENTS

| | | | |
|---|---|---|---|
| 2010/0262002 A1* | 10/2010 | Martz | A61M 5/14566 600/432 |
| 2010/0274180 A1* | 10/2010 | Donovan | A61B 17/8872 604/65 |
| 2010/0286619 A1* | 11/2010 | Abry | A61M 5/2033 604/192 |
| 2011/0270027 A1* | 11/2011 | Augarten | A61M 5/486 600/37 |
| 2011/0270131 A1* | 11/2011 | Snow | A61F 5/0056 600/587 |
| 2012/0071819 A1 | 3/2012 | Bruggemann et al. | |
| 2012/0143117 A1* | 6/2012 | Perry | A61B 3/16 604/8 |
| 2013/0274655 A1 | 10/2013 | Jennings et al. | |
| 2013/0280687 A1* | 10/2013 | Edwards | G06Q 10/00 434/262 |
| 2013/0338576 A1 | 12/2013 | O'Connor et al. | |
| 2014/0012229 A1 | 1/2014 | Bokelman et al. | |
| 2014/0155827 A1 | 6/2014 | Ostrander et al. | |
| 2014/0207106 A1 | 7/2014 | Bechmann et al. | |
| 2014/0236076 A1 | 8/2014 | Marshall et al. | |
| 2014/0249410 A1 | 9/2014 | Uber, III et al. | |
| 2015/0297833 A1* | 10/2015 | Henderson | A61M 5/2033 604/135 |
| 2016/0074587 A1* | 3/2016 | Searle | G01R 33/072 604/189 |

\* cited by examiner

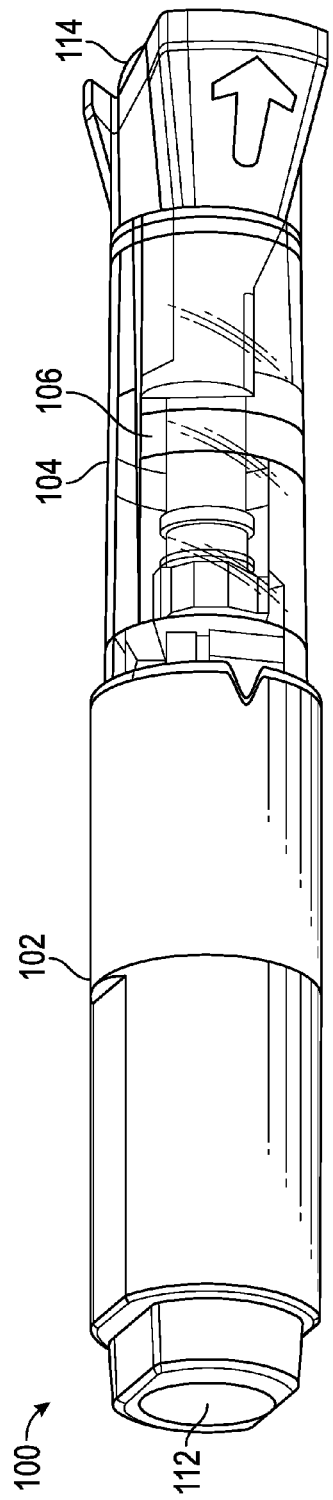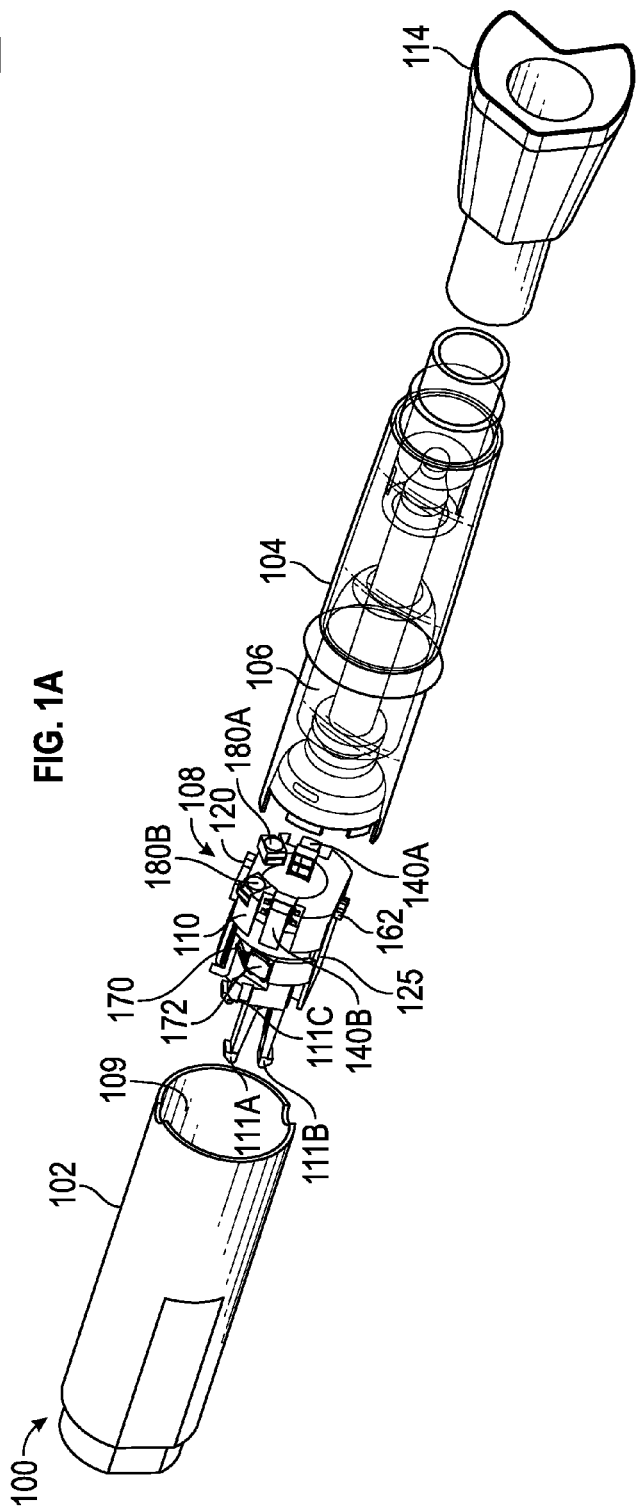

SMART MODULE FOR INJECTION DEVICES

RELATED U.S. APPLICATIONS

This application claims priority to U.S. Provisional Appl. No. 62/104,593 filed on Jan. 16, 2015 and U.S. Provisional Appl. No. 62/248,984 filed on Oct. 30, 2015, each of which are incorporated by reference in their entirety.

BACKGROUND OF THE INVENTION

Field of the Invention

This invention relates to injection devices, and more particularly, relates to smart autoinjectors for injecting liquid medicines into patients in need of therapeutic treatments.

Description of the Related Art

Autoinjectors are medical devices that allow patients to self-administer their medications outside a hospital or physician's office. These devices are often used for the management of chronic diseases. A typical autoinjector consists of a prefilled syringe in a mechanical device that deploys a needle and delivers a medicament with a single push of a release button. Autoinjectors may also be disposable, and can include safety mechanisms to shield the needle both before and after injection.

An autoinjector, or its contents, may be damaged during the manufacturing or delivery process. For example, the autoinjector can be damage during transportation, storage, or immediately before or after use. The medicine may be damaged by being subjected to high or low temperatures, pressures, or other extreme environmental conditions. A patient self-administering medication using an autoinjector may be unaware of any the damage, and therefore can be at risk for administering outdated or improperly stored medicine. The patient may also be at risk for using an autoinjector that has been physically damaged and shouldn't be used for treatment. To overcome some of these disadvantages, prior autoinjectors have included a viewing window to provide a patient visual access to the medicament and the injection mechanisms. However, visual access alone may not alert a patient to certain defects in the device or the medicament. Similarly, visual access alone may not be sufficient to inform the user of the status of the injection, for example if the drug was injected fully and the injection is complete.

SUMMARY OF THE INVENTION

One aspect of the invention is a smart module device that can detect the condition of use of an injection device and communicate that information to a patient. In this embodiment, the smart module is configured to fit within, or outside of, the physical structure of a pre-existing injection device and thereby convert the pre-existing device into a smart device.

One embodiment is a module for detecting environmental parameters. The module may include: a carrier configured to mate with an injection device; one or more environmental sensors mounted on the carrier, at least one indicator; and a processor configured to read parameters from the environmental sensors and activate the indicator if a predetermined event occurs.

The foregoing and/or other aspects of the present invention are achieved by providing a module containing one or more sensors related to conditions affecting an injection device that can be placed in the interior volume the injection device.

Another embodiment of the present invention is a method for detecting the condition of use of an injection device comprising an injection device with a module placed in the interior volume of the injection device.

In another embodiment of the present invention, data related to the condition of use of an injection device can be transmitted to an external device.

Another embodiment is a method of detecting activation of an injection device. The method may include: providing an injection device configured to administer a medicament; providing a module comprising a processor, wherein the module attaches to the injection device and is configured to detect environmental parameters using one or more one or more environmental sensors communicating with the processor; and activating an indicator on the module if a predetermined event is detected.

BRIEF DESCRIPTION OF THE DRAWINGS

FIG. 1A depicts an injection device with a module in accordance with an illustrative embodiment of the present invention.

FIG. 1B depicts an exploded perspective view of an injection device with a module in accordance with an illustrative embodiment of the present invention.

DETAILED DESCRIPTION

Figure 2A:
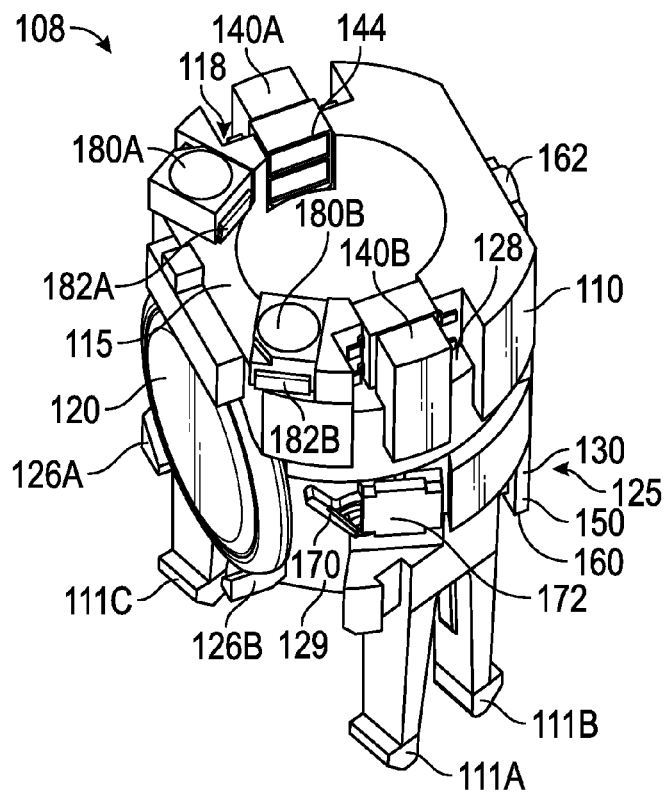
FIG. 2A depicts a module in accordance with an illustrative embodiment of the present invention.

As will be appreciated by one skilled in the art, there are numerous ways of carrying out the examples, improvements, and arrangements of a medicament delivery device in accordance with embodiments of the invention disclosed herein. Although reference will be made to the illustrative embodiments depicted in the drawings and the following description, these embodiments are not meant to be exhaustive of the various alternative designs and embodiments that are encompassed by the disclosed invention. Those skilled in the art will readily appreciate that various modifications may be made, and various combinations can be made, without departing from the invention.

Embodiments of a smart module, or an autoinjector including the smart module, or a patch injector including the smart module, are depicted in FIGS. 1-15. One embodiment is a smart module that is designed to fit within an interior volume of an injection device, such as an autoinjector or patch injector. For example, the smart module may be adapted to fit within the interior space of a PHYSIOJECT™ autoinjector from Becton Dickinson®. In this embodiment, the smart module is configured to fit entirely within the interior of the injector, and does not add to the size or exterior form factor of the injector. The smart module may also be adapted to fit within the interior space of a LIBERTAS™ patch injector from Becton Dickinson®. As used herein, the term "smart module" and "module" are used interchangeably.

In an illustrative embodiment the smart module can include one or more sensors capable of monitoring and detecting external events or characteristics associated with the use of an injection device. Sensing can be performed by contact and/or non-contact methods, including but not limited to microswitch sensing, electrostatic sensing, capacitive sensing, optical sensing, infrared (IR) sensing, and magnetic sensing. These sensors can be configured to measure temperature, pressure, motion, orientation or electromagnetic radiation, such as light, capacitance, and inductance, of an autoinjector. The module may detect the state and function of the injection device at any time including after manufacture, during storage, during transportation, immediately before use of the injection device, during use of the injection device, and after use of the injection device. The module can also include a microprocessor configured to process data from the sensors to determine a state of the device. Once a state of the device is determined, the microprocessor may determine if the device is ready-to-use or not-ready for use by a patient.

The processor may be programmed or configured to determine if a sensor has detected a parameter that is outside of a predetermined boundary or range. For example, the safe storage temperature for a drug may be from 35° F. to 50° F. Thus, if the temperature sensor in the smart module detects a temperature that is outside of this range, the processor may be configured to activate an indicator light warning the patient that the drug in the autoinjector may not be safe. Similarly, the processor may be programmed to analyze a plurality of conditions, such as temperature, and the amount of time at each temperature. Accordingly, if the autoinjector is detected to only be outside of the safe range for a limited period of time, for example one minute, then the processor may not activate the indicator. Other combinations of sensor measurement, and analysis by the processor are within the scope of the invention so that the indicators are activated to warn the user based on predetermined measurements and processes designed to notify the patient of that the autoinjector may have been subject to potential harmful conditions affecting the efficacy of their medicine.

In some embodiments, the smart module is configured to have enough power and battery life so that it can detect weeks, months, or years for sensor data during transportation and storage. Accordingly, the smart module may be initialized and placed within an autoinjector during or after manufacturing. From that point forward, the smart module may capture and store sensed environmental parameters to an onboard memory. The smart module may be configured to take environmental parameter readings hourly, daily, weekly or on any other predetermined schedule based on the available power in the device. In other embodiments, the smart module may be programmed to have a varying schedule for capturing environmental conditions. For example, in the first month after manufacture, when the device is most likely to be transported to a user, the module may be programmed to sample environmental parameters every hour. After the first month, the module may be programmed to sample environmental parameters on a less-frequent basis, such as every day, or ever few days.

In an illustrative embodiment according to the present invention, the smart module may also include status indicators to provide an indication to a user of the condition of the device. The status indicators may be in the form of visible, audible, and haptic indicators that transmit light or other visual, auditory or tactile stimuli to notify the user of a condition or state of the device. For example, a red indicator light on the smart module may become activated to indicate that the autoinjector should not be used. Additionally, an auditory signal, such as a beep or chirp may be output from a speaker on the module to indicate that the device has been damaged in some way prior to use. Vibration or tactile status indicators on the smart module may vibrate at predetermined intervals to indicate that the device has been damaged.

In an illustrative embodiment according to the present invention, the smart module may further include a communication module to allow for connectivity between the injection device and external devices, allowing information from the module to be transmitted to interested parties including the patient, payers, pharmacies and clinicians. For example, prior to use, the smart module may be connected to an application running on a portable electronic device, such as a smart phone or tablet. This connection may be made using well-known wireless communication protocols, such as Bluetooth, WIFI, or other means. Once the application detects a connection to the smart module, data from the on-board sensors may be transmitted to the application for display to the user. For example, the highest and lowest measured temperature of the device during transport may be displayed. In other embodiments, a chart or graph showing the measured environmental parameters may be displayed to the user. For example, a temperature graph illustrating the daily maximum temperature measured by the smart module may be displayed to the user.

As mentioned above, the smart module may be configured and shaped to retrofit a pre-existing injection device. The module may be placed within an injector so that the structure of the pre-existing injection device can be used to initiate features of the module. For example, the smart module may include an electronic switch or lever that is activated once the user activates the push button that releases the autoinjector needle. In this regard, the module would be placed within the autoinjector so that the placement of the module does not prevent activation or movement of any of the pre-existing functions of the injection device.

Thus, in one embodiment the smart module can detect when the autoinjector has been activated by the user to administer medicine. This allows additional functionality to be designed into the smart module. For example, upon detection of the activation event, the smart module can transmit a signal to any connected external device. The external device may be a computer, or portable electronic device that records the time and date of the activating in order to help the user track when the injections have taken place.

In one embodiment, the smart module is placed within an autoinjector that is configured to administer a single dose of a drug to a patient. Representative examples of drugs that may be used in such an autoinjector include ORENCIA® and HUMIRA®. Upon administration the smart module may detect the injection event, and transmit a signal to a software program that tracks injection information for the patient. This would provide a simple and efficient mechanism that allows a patient to track a day and time of their injections, which may be beneficial for patients undergoing an extensive medical regimen. In some embodiments, the smart module may detect the amount of drug given from the autoinjector to verify completion of a dose.

In an illustrative embodiment, the injection device may be disposable. In some embodiments of the present invention, the module may be disposable as well. In other embodiments, the module may be removed and placed in a different disposable injection device to convert it into a smart injector device. In some embodiments, the smart module includes a reset function or button that erases the prior sensor data, and allows the module to be placed within a new autoinjector with no prior sensor history.

Although various persons, including, but not limited to, a patient or a healthcare professional, can operate or use illustrative embodiments of the present invention, for brevity an operator, patient or user will be referred to as a "user" hereinafter.

Although various fluids can be employed in illustrative embodiments of the present invention, fluid in an injection device will be referred to as "medicament" hereinafter.

Although various inputs, including, but not limited to, mechanical buttons, tactile inputs, voice-controlled input, or any other inputs known in the art, can be implemented using illustrative embodiments of the present invention, for brevity an input will interchangeably be referred to as a "button" or a "trigger" hereinafter.

FIG. 1A depicts an illustrative embodiment of an injection device 100. The injection device 100 includes an upper portion 102 and a lower portion 104. The upper portion 102 includes an activation button 112 that activates the autoinjector to release a syringe into a user. Thus, when the activation button 112 is engaged, the syringe inside the lower portion 104 is deployed so that medicament is injected into a user.

The lower portion 104 includes a transparent viewing window 106 that allows the patient to see the internal mechanisms within the injection device 100. At the distal end of the lower portion 104 is a safety cap 114 configured to prevent the user from inadvertent contact with the syringe.

A smart module 108 (not shown) is located in the interior volume of the upper portion 102 of the injection device 100. The smart module mates with the upper portion 102 of the injection device 100 but does not disrupt the normal operation of the injection device 100.

In an illustrative embodiment according to the present invention, the viewing window 106 allows for a user to view one or more status indicators located in the interior volume of the injection device 100. The one or more status indicators may be part of the module and can indicate a condition or state of the device. The status indicators may include one or more lights, such as light-emitting diodes "(LEDs") or any other visual, auditory, or tactile stimuli. The condition or state of use may include, but is not limited to, ready-to-use, not-ready, and fault, refrigerated, warming up, inside packaging, or outside of packaging. Visual stimuli may include varying color patterns to indicate different conditions or states of use. Visual stimuli may also include various lengths of light radiation. For example, one or more lights may radiate for a first amount of time to indicate the device is ready-to-use and a second amount of time to indicate that the device is not-ready. Visual stimuli may also include various patterns of light radiation. For example, one or more lights may radiate a particular number of times to indicate different conditions or states of use of the device, such as multiple light radiations in short succession to indicate ready-to-use and a single light radiation to indicate not-ready.

The status indicators may also include one or more speakers configured to produce auditory stimuli. Different auditory stimuli can indicate different conditions or states of the device, including, but not limited to, include, but is not limited to, ready-to-use, not-ready, and fault, refrigerated, warming up, inside packaging, or outside of packaging. Each auditory stimulus can include one or more tones. Multiple tones may be used in combination or in series. Tones for each auditory stimulus may also vary in pitch, volume, and duration. In some embodiments, an auditory stimulus can include a voice recording reciting one or more conditions or states of the device.

FIG. 1B depicts an exploded view of an illustrative embodiment of the injection device 100. The upper portion 102 connects with the lower portion 104 to form the injection device 100. In an illustrative embodiment according to the present invention, the upper portion 102 and lower portion 104 can be detached, and a smart module 108 can be placed inside an interior volume 109 of the upper portion 102 of the injection device 100. As shown the smart module 108 has a carrier 110 that has an upper set of tangs 111A,B,C,D (tang D not shown). The upper tangs 111A,B,C,D protrude into the interior volume 109 and mate with a tab (not shown) inside of the upper portion 102.

The smart module 108 also includes a battery 120 on a first side of the carrier 110, an electronics package 125 on an opposite side of the carrier 110, a set of status indicators 180A,B, a set of optical (IR) sensors 140A,B, an ambient light photodiode sensor 162, a microswitch 170, and a microswitch mounting brace 172.

After placement of the module 108, the upper portion 102 and lower portion 104 can be reconnected so that the module 108 is positioned inside of the injection device 100.

It should be realized that the injection device 100 can function to inject medicament into the user without the presence of the module 108 in one embodiment, and the module 108 adds electronic monitoring and reporting capabilities to the pre-existing device. Thus, the module 108 can be placed in the interior volume of an injection device 100 after manufacture, without changing the exterior size or form of the injection device 100 or preventing the function of the injection device 100. Alternatively, the module 108 can be placed in the interior volume of the injection device 100 during the manufacturing process. In an illustrative embodiment according to the present invention, the injection device 100 is a PHYSIOJECT' injector manufactured by Becton Dickinson®. Although it should be realized that other injector devices are also contemplated within the scope of the invention.

Figure 2B:
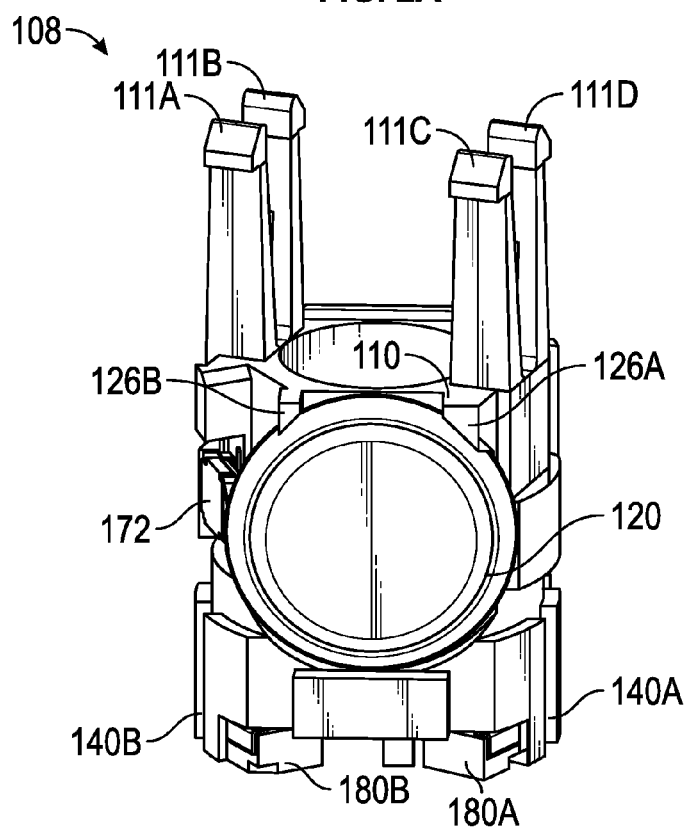
FIG. 2B depicts a module in accordance with an illustrative embodiment of the present invention.

FIGS. 2A and 2B depict a more detailed embodiment of the smart module 108. The module 108 comprises the carrier 110 which is cylindrical in shape and has openings for the separate parts of the module 108. Mounted into a set of rounded channel pieces 126A,B on the left side of the module 108 is the battery 120. The battery 120 is mounted into the set of channel pieces 126A,B by electrical connections (not shown) which provide power to the remaining portions of the module 108. It should be realized that the set of channel pieces 126A,B are configured so that the manufacturer can mount the battery 120 while still allowing the module 108 to fit within a cylindrical housing.

Opposite of the battery 120, on the right side of the carrier are the electronics package 125 and the ambient light photodiode sensor 162. The electronics package 125 is mounted in a rectangular channel (not shown) carved out from the right side of the cylindrical carrier 110. In this embodiment, the electronics package includes a nonvolatile memory 130, a microprocessor 150, and a communication module 160. It should be realized that the rectangular channel on the right side of the carrier 110 is configured so that the manufacturer can mount the electronics package 125 while still allowing the module 108 to fit within a cylindrical housing. Thus, although the module 108 is not perfectly cylindrical, it includes channels within the cylindrical carrier 110 for the necessary electronic parts such that they are recessed below a cylindrical outline that would be created by the carrier 110 if it had not had electronics mounted on its sides.

The electronics package 125 further comprises a memory 130, a microprocessor 150, and a communication module 160.

Mounted into a rectangular channel 129 on the front of the module 108 is a microswitch 170 and a microswitch mounting brace 172. It should be realized that the rectangular channel 129 is configured so that the microswitch 170 and the mounting brace 172 do not protrude from the circumferential design of the module 108, and thus can allow the module 108 to fit within a cylindrical housing, such as for an injector device.

Mounted on a top surface 115 of the module 108 are status indicators 180A,B. The status indicators 180A,B may illuminate to notify the user of predetermined conditions of the injector, as discussed in more detail below. For example, the status indicators 180A,B may be LED or other type of light-emitting modules. It should be realized that the status indicators 180A,B can be configured so that the module 108 can fit within a cylindrical housing. The status indicators 180A,B further comprise electrical connectors 182A,B. Mounted on the rear and front sides of the carrier 110 are the optical (IR) sensors 140A,B. The optical (IR) sensors 140A,B are mounted in channels 118 and 128 respectively so as to allow the module 108 to fit within a cylindrical housing. A back-plate 144 of the optical (IR) sensor 140A is also visible.

As shown, the carrier 110 further comprises the upper pair of tangs 111A,B,C,D. The upper pair of tangs 111A,B,C,D are configured to mate with a tab inside the upper portion of an autoinjector. This mating allows the carrier 110 to reversibly mount to the interior of an autoinjector.

The carrier 110 houses the battery 120, the memory 130, the optical (IR) sensors 140A,B, the ambient light photodiode sensor 162, the microprocessor 150, the communication module 160, the microswitch 170, and the status indicators 180A,B. The optical (IR) sensors 140A,B, ambient light photodiode sensor 162, and the microswitch 170 are in communication with the microprocessor 150. The microprocessor 150 is further in communication with the memory 130, the communication module 160, and the status indicators 180A,B.

In an illustrative embodiment according to the present invention, the module 108 is shaped so that the existing design of an injection device holds the module 108 in place and allows for activation of the micro-switch 170 when a button or other trigger of the injection device is activated. In operation, the module 108 allows for activation data or sensor data to be recorded, transmitted, or indicated through a series of steps.

The module 108 is configured to monitor and detect events and characteristics associated with the use of an injection device. The module 108 can also communicate various conditions and states of the injection device to a user through visual, auditory, or tactile stimuli or can transmit that data to an external device.

In an illustrative embodiment according to the present invention, the activation data comprises the time that the microswitch 170 is activated. In an illustrative embodiment according to the present invention, the microswitch 170 can be activated at the time that an injection event occurs. The activation data can be recorded, transmitted, or indicated in a series of steps. First, the microswitch 170 is activated. This may occur when a button or trigger on the injection device is engaged. In one embodiment, the microswitch 170 is activated when a button on the injection device that causes medicament to be injected is engaged, such as activation button 112 of injection device 100. In response, activation data is transmitted from the microswitch 170 to the microprocessor 150.

From the microprocessor 150, the activation data can be one or more of stored in the memory 130, transmitted through the communication module 160, and indicated by the status indicators 180A,B. The communication module 160 can be connected to a network to transmit activation data to an external device. The status indicators 180A,B can display to a user that the microswitch 170 has been activated. This may occur through a visual, auditory, or tactile indication. In one embodiment, the status indicators 180A,B comprise one or more (LEDs). The one or more of the LED's may be activated, and consequently, emit light to indicate that the microswitch was activated. In an alternative embodiment, the status indicators comprise one or more speakers.

In an illustrative embodiment according to the present invention, sensor data may also be recorded, transmitted, or indicated through a series of steps. The optical (IR) sensors 140A,B and the ambient light photodiode sensor 162 can collect parameter data including but not limited to temperature, light, motion, orientation, and amount of medicament present. In one illustrative embodiment according to the present invention, the optical (IR) sensors 140A,B and the ambient light photodiode sensor 162 are activated when microswitch 170 is activated. In response, sensor data is transmitted from the optical (IR) sensors 140A,B and the ambient light photodiode sensor 162 to the microprocessor 150. The microprocessor 150 then performs on-board processing using an algorithm to determine a current state of the device. In one embodiment, the microprocessor determines whether one or more parameters are located outside of a defined range. Examples of state of the device determinations include, but are not limited to, ready-to-use, not-ready, fault, refrigerated, warming up, inside packaging, or outside of packaging.

The state of the device data can be transmitted from the microprocessor 150 to the memory 130, in which the data can be stored. The state of the device data can also be transmitted from the microprocessor 150 to the communication module 160. After receiving the state of the device data, the communication module 160 can transmit the data to an external device. After the state of the device is determined, the microprocessor 150 can also communicate with the status indicators 180A,B. In response, the status indicators 180A,B can indicate the state of the device to a user. For example, when the status indicators comprise one or more LEDs, one or more of the LEDs may be activated and emit light in response to the state of the device determination. For example, when the device is taken out of the refrigerated storage and is warming up to be used, the LEDs may signal to the user the progression of the temperature as it approaches and reaches a ready-to-inject value. The sensor data can also be stored in the memory 130 or transmitted to an external device.

In an alternative embodiment, the optical (IR) sensors 140A,B are activated when the module 108 is placed inside the injection device. The optical (IR) sensors 140A,B and the ambient light photodiode sensor 162 can collect data at any time including after manufacture, during storage, during transportation, immediately before use of the injection device, during use of the injection device, and after use of the injection device. In one embodiment, the sensor data is periodically recorded in the memory 130 and transmitted to an external device by the communication module 160. In an alternative embodiment, when sensor data is collected, the microprocessor 150 performs on-board processing using an algorithm to determine a current state of the device. The state of the device can be stored in the memory 130 or transmitted to an external device by the communication module 160. After the state of the device is determined, the microprocessor 150 can also communicate with the status indicators 180A,B. In response, the status indicators 180A,B can indicate the state of the device to a user.

In an alternative embodiment, sensor data can be recorded, transmitted or indicated both before and after activation of the microswitch 170. In one embodiment, one or more of the optical (IR) sensors 140A,B and the ambient light photodiode sensor 162 can collect data when the module 108 is placed inside the injection device, before activation of the microswitch 170. Therefore, the state of the device can be determined at any time including after manufacture, during storage, during transportation and immediately before use of the injection device. In one embodiment, the sensor data can be stored in the memory 130 or transmitted to an external device by the communication module 160. The sensor data may also be processed by the microprocessor 150 using an algorithm to determine the state of the device. The state of the device can be stored in the memory, transmitted to an external device, or indicated by the status indicators 180A,B. At a later time the microswitch 170 can be activated.

After the microswitch 170 is activated, activation data and data from one or more of the one or more sensors can be collected, stored in the memory 130, and transmitted to an external device by the communication module 160. The activation data and sensor data can also be processed in the microprocessor 150 to determine a state of the device. This allows the state of the device determination to be updated at the time of injection from the previous state of the device determination based on pre-injection sensor data. In this embodiment, the microprocessor can utilize data from both before injection and at the time of injection to determine a current state of the device. The state of the device can be recorded in the memory 130, transmitted to an external device by the communication module 160, or indicated by the status indicators 180A,B.

In an alternative embodiment, the optical (IR) sensors 140A,B and the ambient light photodiode sensor 162 can be initiated through the use of an external device. The external device can communicate with the communication module 160 of the module 108. In response, the optical (IR) sensors 140A,B and the ambient light photodiode sensor 162 can be activated and can detect data relevant to condition or state of the device. In one embodiment, external device is a mobile device running a software application.

In an illustrative embodiment according to the present invention, the carrier 110 can comprise plastic, but other materials are also possible.

In an illustrative embodiment according to the present invention, the battery 120 is a CR1025 coin cell battery. In one embodiment, the battery 120 can include an external switch. The battery 120 supplies power to the module 108.

It should be recognized that the sensors 140A,B are not limited to optical (IR) sensors and that the sensor 162 is not limited to an ambient light photodiode sensor. Sensors 140A,B and sensor 162 can comprise any sensor capable of detecting environmental conditions or conditions of use of an injection device. Sensing can be performed by contact and/or non-contact methods, including but not limited to microswitch sensing, electrostatic sensing, capacitive sensing, optical sensing, infrared (IR) sensing, and magnetic sensing. Illustrated examples are discussed below.

In an illustrative embodiment according to the present invention, the sensors 140A,B and the sensor 162 may comprise a temperature sensor. In one embodiment, the temperature sensor can be used to verify cold-chain storage and distribution. In one embodiment, the temperature sensor can be used to detect the ambient temperature when an injection event occurs. In one embodiment, the temperature sensor is a thermistor. In one embodiment, the thermistor is a thermistor built into a TI CC2540 Bluetooth microcontroller. When uncalibrated, this thermistor can allow temperature accuracy within +/−10° C. of the actual temperature. When calibrated the temperature accuracy can be improved to be within +/−5° C. of the actual temperature. In an alternative embodiment, the temperature sensor can be attached externally to the module 108. This temperature sensor can be a thermistor. When attached externally, a thermistor can detect a temperature within 0.5° C. to the actual temperature. This temperature range is appropriate for monitoring medicament exposure and injection device exposure to temperatures outside of normal storing conditions. In some embodiments, normal storing conditions are between 2°–8° C.

In an illustrative embodiment according to the present invention, the sensors 140A,B and the sensor 162 can comprise a light sensor including, but not limited to, an ambient light photodiode sensor. The light sensor can detect if a medicament has been exposed to light, as light can potentially spoil a medicament.

In an illustrative embodiment according to the present invention, the sensors 140A,B and the sensor 162 can comprise an optical sensor including, but not limited to, an optical (IR) sensor. An optical sensor can detect data relevant to end of dose. In another embodiment, the one or more sensors can detect dose administration speed.

In an illustrative embodiment according to the present invention, the sensors 140A,B and the sensor 162 can comprise a Hall effect sensor. A Hall effect sensor can detect data relevant to end of dose.

In an illustrative embodiment according to the present invention, the sensors 140A,B and the sensor 162 can include a motion sensor. A motion sensor can detect data relevant to an intent to inject or to the orientation of the device.

In an illustrative embodiment according to the present invention, the sensors 140A,B and the sensor 162 can include a flow sensor. This sensor can detect dose administration speed and end of dose.

In an illustrative embodiment according to the present invention, the sensors 140A,B and the sensor 162 can identify the type of medicament in the injection device.

In an illustrative embodiment according to the present invention, the sensors 140A,B and the sensor 162 can include a location sensor such as GPS technology for determining the location of a user at the time of an injection event.

In an illustrative embodiment according to the present invention, the status indicators 180A,B can comprise one or more LEDs. The status indicators 180A,B can notify a user of a condition or state of the device. Examples of conditions or states of the device include, but are not limited to, ready-to-use, not-ready, fault, refrigerated, warming up, inside packaging, or outside of packaging. The one or more LEDs may indicate different conditions to a user through color, duration, or the repetition of light emission. In one embodiment, a steady green light would indicate to a user that all conditions necessary for administering a dose are met and that the dose is ready to be administered.

The communication module 160 can be connected to a network by wired or wireless communication, cell communication, Bluetooth®, ZigBee®, LAN, WLAN, RF, IR, or any other communication method or system known in the art. The communication module 160 can communicate with a mobile device, a home health monitor, a computer, a server, or any other external device. This allows device data to be transmitted to users, payers, pharmacists, physicians, nurses, family members or any other desired parties.

In an illustrative embodiment according to the present invention, the communication module 160 is a BLE113 radio (Bluegiga Technologies, Duluth, Ga.). The BLE 213 radio transfers data through Bluetooth® connectivity. In one embodiment, the communication module 160 communicates data through Bluetooth® to a mobile device running a software application. In another embodiment, the communication module 160 communicates data through Bluetooth® to a home health monitor with cloud connectivity. In one embodiment, the device data is transmitted to an external device of a user, and the user determines if they would like to forward the information to payers, pharmacists, physicians, nurses, or other third parties. In one embodiment, the external device is a mobile device running a software application, and the software application allows a user to choose to whom the user would like to transmit data. In an alternative embodiment, the device data is transmitted directly to payers, pharmacists, physicians, nurses, or other third parties.

It should be realized that although the module 108 is shown to be designed to be fully integrated in the interior of an injection device, embodiments of the invention are not limited to internal smart modules. For example, an alternate embodiment may include a smart module with features that are similar to the module 108, but designed to mount to the outer shell of an autoinjector. In this embodiment, the device may be cylindrical in shape, and configured to reversibly mount to the exterior shell or cap of an autoinjector. In one embodiment, the smart module may include tabs, snaps, brackets or other means for mounting to the outside of an autoinjector. In one embodiment, the device may include an activation switch that is configured to be activated when the autoinjector device is used. Such a switch could connect to, cover, or adhere to, the activation switch that is on the autoinjector.

Figure 3:
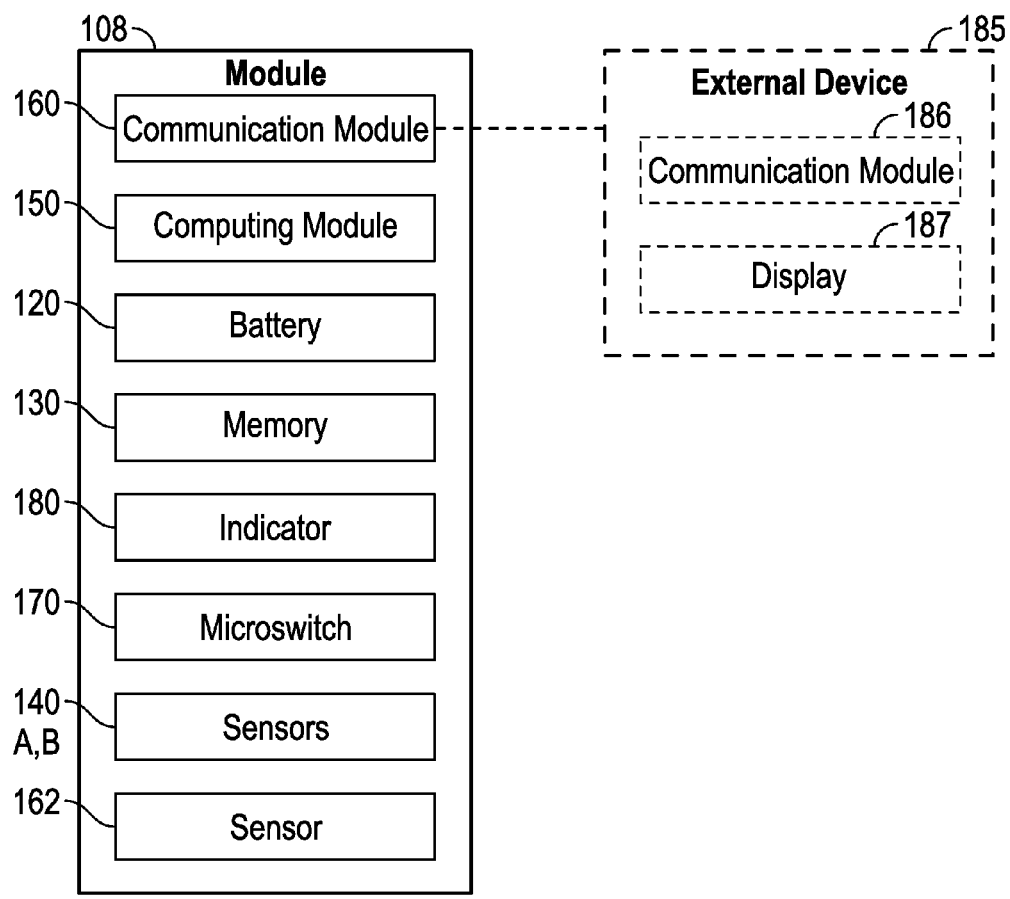
FIG. 3 depicts a schematic view of a module in accordance with an illustrative aspect of the present invention.

FIG. 3 depicts a schematic view of an illustrative embodiment of the module 108. The module 108 comprises a battery 120, a nonvolatile memory 130, sensors 140A,B, sensor 162, a microprocessor 150, the communication module 160, microswitch 170, and status indicators 180A,B.

In an illustrative embodiment according to the present invention, the communication module 160 can be connected to a network by wired or wireless communication, cell communication, Bluetooth®, ZigBee®, LAN, WLAN, RF, IR, or any other communication method or system known in the art. The communication module 160 can communicate with an external device 185 such as a mobile device, home health monitor, computer, server, or any other electronic external device that is known in the art. This allows device data to be transmitted to users, payers, pharmacists, physicians, nurses, family members or any other desired parties. In one embodiment, the external device includes a communication module 186 for receiving data from the communication module 160. In one embodiment, the external device includes a display 187 to allow a user to read data on the external device. In one embodiment, the external device is a mobile device, such as a mobile telephone or tablet running a software application. In one embodiment, the external device receives data from the communication module 160 and after receiving the data, transmits the data to another location, such as a server computer.

Figure 4A:
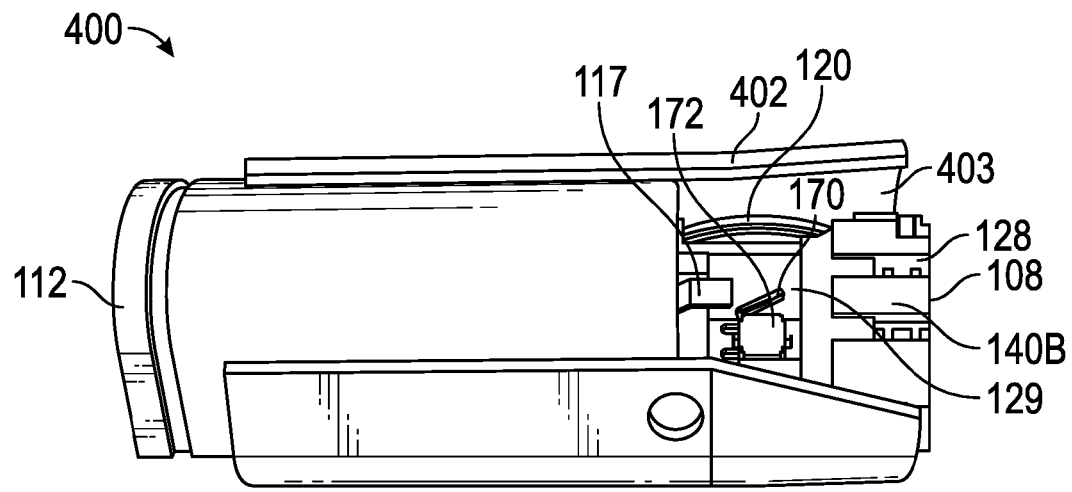
FIG. 4A depicts a sectional view of an injection device in accordance with an illustrative embodiment of the present invention.
Figure 4B:
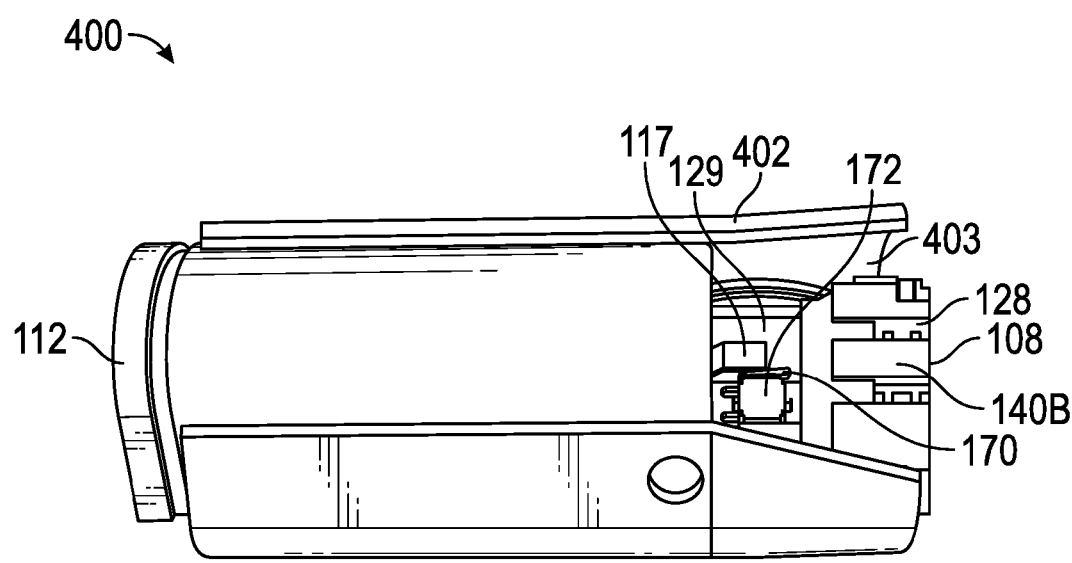
FIG. 4B depicts a sectional view of an injection device in accordance with an illustrative embodiment of the present invention.

FIGS. 4A and 4B depict an illustrative embodiment of a cut-away section 400 of the injection device 100 according to the present invention. The section 400 shows a section 402 of the upper portion 102 of the injection device 100. The activation button 112 extends along the interior of the section 402 in a cylindrical channel 403. The cylindrical channel 403 further houses the module 108. The activation button 112 further comprises a protrusion 117 that extends outwards towards the module 108. The microswitch 170, the mounting brace 172, the rectangular channel 129, the channel 128, the optical (IR) sensor 140B and the battery 120 of the module 108 are also shown.

The activation button 112 can interact with the microswitch 170 of the module 108. When the activation button 112 is engaged by the user, the activation button 112 and the protrusion 117 move along a cylindrical channel towards the module 108. As a result of the movement, the protrusion 117 engages and contacts the microswitch 170. As a result, microswitch 170 is activated.

FIG. 4A shows a section of an injection device 100 before the activation button 112 is engaged. FIG. 4B shows a section of an injection device 100 after the activation button 112 is engaged. In FIG. 4B, the microswitch 170 is contacted by the protrusion 117 and therefore engaged.

In one embodiment, engaging the activation button 112 also causes an injection event to occur within the injector. In an alternative embodiment, the microswitch 170 can be activated by a button that does not cause an injection event to occur. In alternative embodiments, the microswitch 170 may be activated by shaking the injection device 100, by orienting the injection device 100 in a predetermined direction, by rotating a portion of injection device 100 in relation to the rest of injection device 100, or by any other mechanical input. In another alternative embodiment, the microswitch can be activated in response to a communication from an external device.

Figure 5:
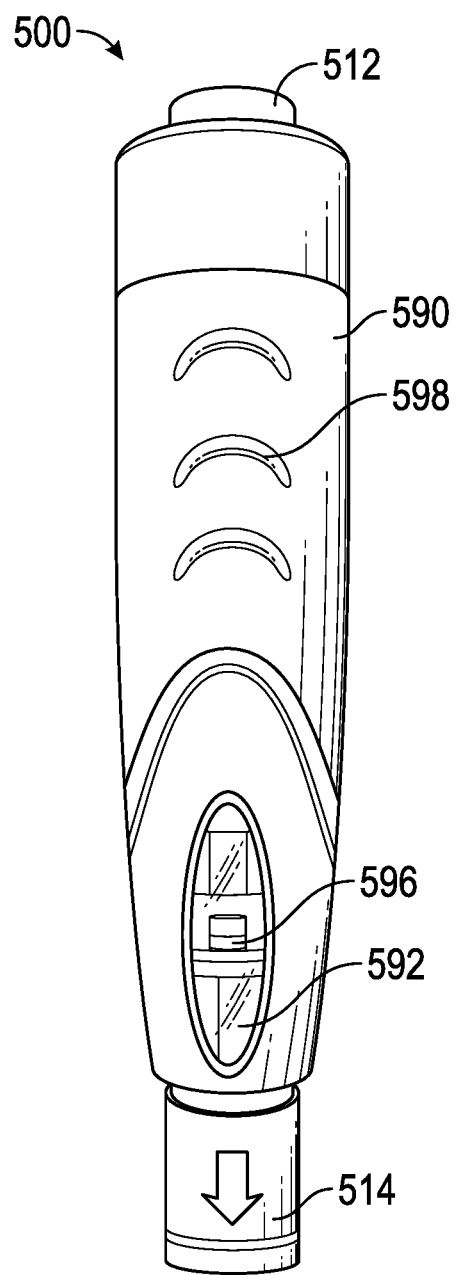
FIG. 5 depicts an injection device with a module in accordance with an illustrative embodiment of the present invention.

FIG. 5 depicts an illustrative embodiment of an injection device 500 according to the present invention. The injection device 500 comprises the same features as the injection device 100 and further comprises a cover 590. An activation button 512 and a safety cap 514 are also shown.

The cover 590 is oriented over the exterior of the injection device 500. The cover 590 comprises a transparent viewing window 592. A syringe component 596 is visible through the viewing window 592. The viewing window 592 also allows a user to observe the visual indication from one or more status indicators (not shown) mounted to a module integrated in the interior of the injection device 500, such as module 108. In one embodiment, the status indicators are oriented so that light emitted from the status indicators radiates in the direction of the viewing window 592, allowing the light to be seen through the viewing window 592.

The cover 590 can provide a protective exterior for injection device 500. The cover 590 can also provide for ergonomic comfort. The cover 590 further includes a set of handgrips 598.

In operation, injection device 500 can perform essentially the same functions as injection device 100. A module located in the interior volume of the injection device 500 is configured to monitor and detect events and characteristics associated with the use of an injection device. The module can then communicate various conditions and states of the injection device to a user through visual, auditory, or tactile stimuli or can transmit that data to an external device. Visual stimuli can be communicated using the status indicators mounted on the module. The visual stimuli can then be observed through the viewing window 592. The module may be activated when a user engages the activation button 512.

Figure 6:
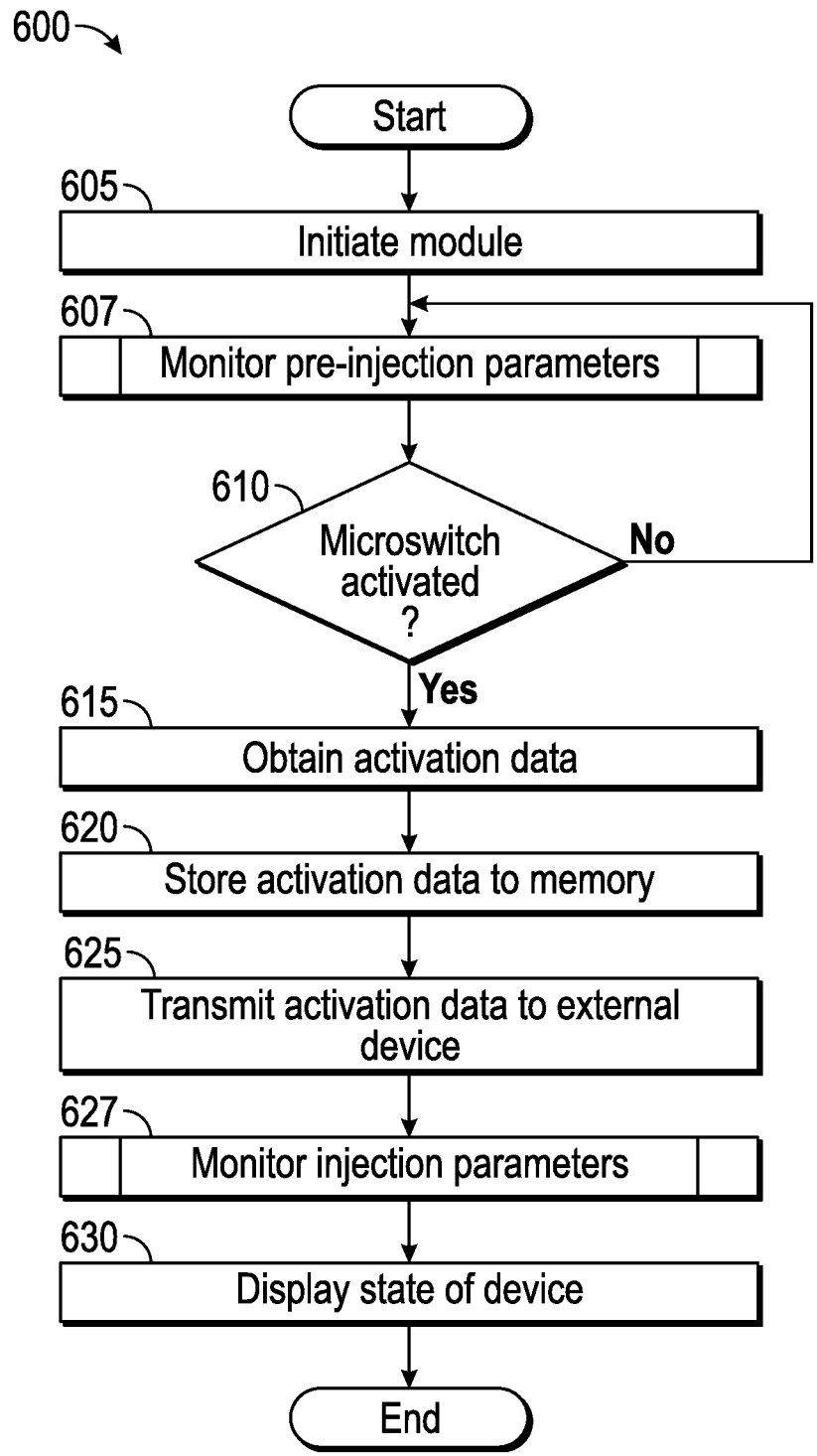
FIG. 6 depicts a flowchart of an embodiment of a system for monitoring the status of an injection device in accordance with an illustrative embodiment of the present invention.

FIG. 6 depicts a flowchart of a process 600 of an illustrative embodiment of a method for monitoring the status of an injection device such as the injection device 100 depicted in FIGS. 1-4b. The process 600 begins at a start step, and then moves to a step 605, wherein a module is initiated, such as module 108 depicted in FIGS. 1-4b. In one embodiment, this occurs when the module is placed in the interior volume of an injection device. However, the module may be initiated any time after manufacture. In an alternative embodiment, the module can be initiated mechanically by a user or operator by pressing a button on the injection device or the module itself, or through any other mechanical input. In an alternative embodiment the module can be activated through in response to a wireless communication received by a communication module of the module.

After initiation, the process 600 moves to a process step 607, wherein pre-injection parameters are monitored by the module. The functions of process step 607 will be explained in further detail below with reference to FIG. 7. After the pre-injection parameters have started to be monitored at process step 607, the process 600 moves to a decision step 610, wherein a determination is made whether a microswitch of the module has been activated. If the microswitch has been activated, the process 600 proceeds to step 615. If the microswitch has not been activated, then the process 600 returns to step 607 to continue monitoring the pre-injection parameters.

A microswitch can be activated as shown in FIGS. 4A-4B. The microswitch can activate in response to a button being engaged on the injection device, such as activation button 112 depicted in FIG. 1, or any other mechanical input, or in response to a wireless communication from an external device. In some embodiments, an injection event will also occur at the time the microswitch is activated.

If a determination has been made at the decision step 610 that the microswitch was activated, then activation data is obtained at the step 615. Activation data can include the time and location at which the microswitch is activated. Activation can also include any other data that is sensed by the module at the time of activation. For example, temperature sensors could capture the temperature of the injector.

In step 620, the activation data is stored in the memory of the module, such as memory 130 depicted in FIG. 2A. The process 600 then moves to a step 625, wherein the activation data is transmitted to any external devices connected to the injector. The transmission can be managed by a communication module, such as communication module 160 depicted in FIG. 2A.

The process 600 then moves to a process step 627, wherein the injection parameters are monitored by sensors of the module. The functions of the process step 627 will be explained in more detail with reference to FIG. 8 below. The process 600 then moves to a step 630, wherein the state of the device is displayed by status indicators of the module, such as status indicators 180A,B depicted in FIG. 2A. In an illustrative embodiment, the state of the device may be displayed by LEDs on the module, the LEDs being visible through a viewing window of the injection device. However, the status indicators can display the state of the device through any visual, auditory or tactile stimuli. In an illustrative embodiment, the state of the device can include, but is not limited to, ready-to-use, not-ready, fault, refrigerated, warming up, inside packaging, or outside of packaging.

Figure 7:
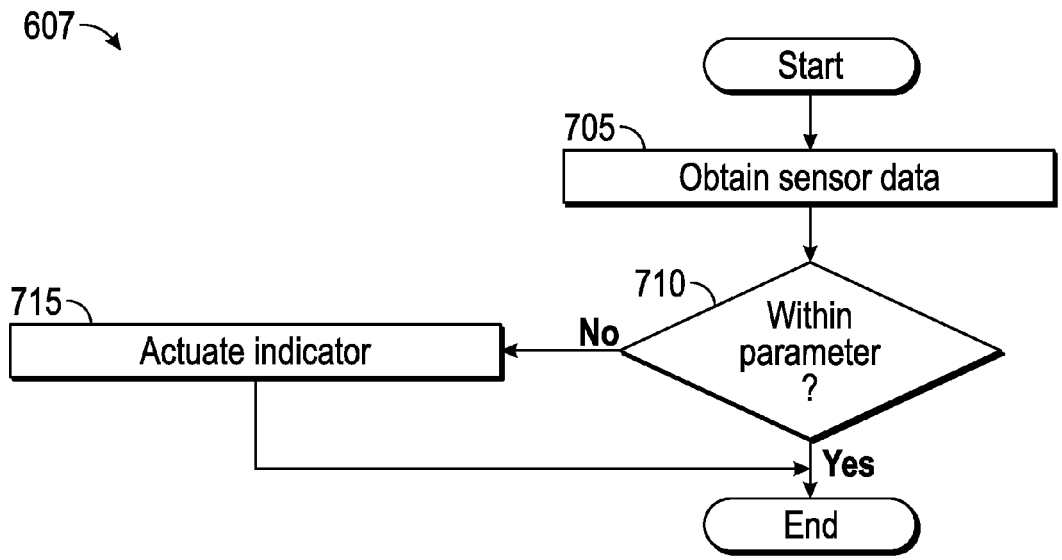
FIG. 7 depicts a flowchart of an embodiment of monitoring sensor parameters in an injection device before injection occurs in accordance with an illustrative embodiment of the present invention.

FIG. 7 depicts a flowchart of the process 607 of an illustrative embodiment according to the present invention of monitoring pre-injection parameters in an injection device. The process 607 begins at a start step, and then moves to a step 705, wherein sensor data is obtained from one or more sensors, such as the optical (IR) sensors 140A,B and the ambient light photodiode sensor 162 depicted in FIG. 2A. The sensors can include but are not limited to a temperature sensor, light sensor, motion sensor, optical sensor, Hall effect sensor, flow sensor or location sensor.

After the sensor data has been obtained, the process 607 moves to a decision step 710, wherein a determination is made whether the sensor data is within a defined set of parameters. The determination can be performed by a microprocessor, such as microprocessor 150 depicted in FIG. 2A. If a determination has been made that the sensor data is within the defined set of parameters, then the process 607 concludes at an end step.

If a determination has been made that the sensor data is outside of the defined set of parameters, then the process 607 moves to a step 715, wherein one or more status indicators of the module are actuated, such as status indicators 180A,B depicted in FIG. 2A. In one embodiment, the status indicators comprise LEDs. However, the status indicators can display the state of the device through any visual, auditory or tactile stimuli. In one embodiment, the one or more sensors comprise a light sensor and a temperature sensor. A determination is made whether the injection device has been exposed to temperature or light outside of a defined range. If the module has been exposed to temperature or light outside of a normal range, the status indicators are actuated. After the status indicators are actuated, the process 607 then concludes at the end step.

Figure 8:
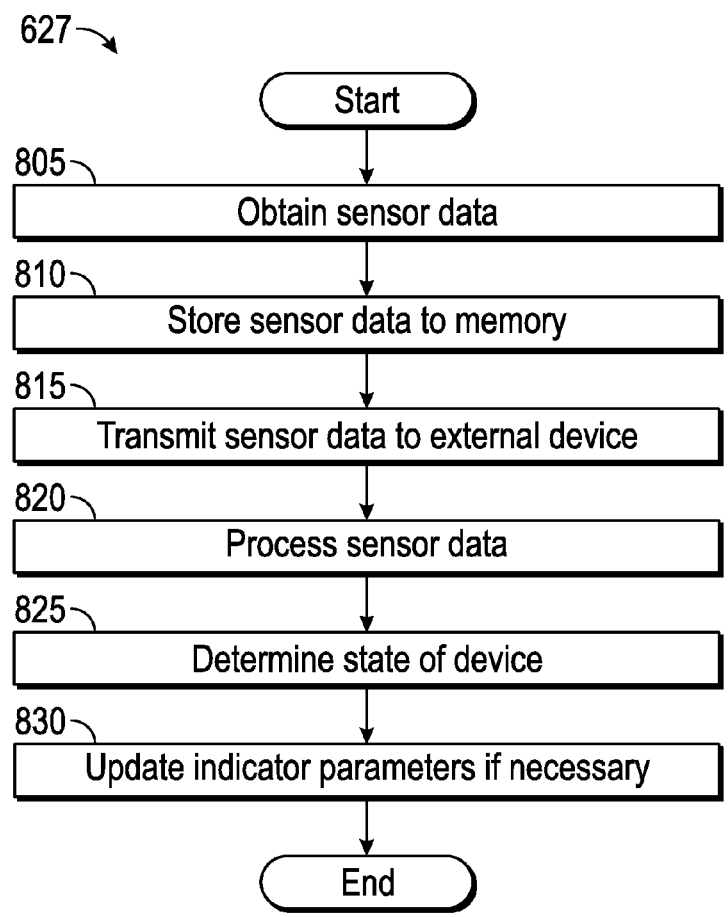
FIG. 8 depicts a flowchart of an embodiment of monitoring sensor parameters in an injection device when injection occurs in accordance with an illustrative embodiment of the present invention.

FIG. 8 depicts a flowchart of the process 627 of an illustrative embodiment of monitoring injection parameters in an injection device. The process 627 begins at a start step, and then moves to a step 805, wherein sensor data is obtained from one or more sensors of a module, such as the optical (IR) sensors 140A,B and the ambient light photodiode sensor 162 depicted in FIG. 2A.

After the sensor data has been obtained, the process 627 moves to a step 810, wherein the sensor data is stored in a memory of the module, such as memory 130 depicted in FIG. 2A. The process 627 then moves to a step 815, wherein the sensor data is transmitted to any external devices connected to the injector. The transmission can be managed by a communication module, such as communication module 160 depicted in FIG. 2A.

The process 627 then moves to a step 820, wherein the sensor data is processed by a microprocessor, such as microprocessor 150 depicted in FIG. 2A. In one embodiment of the step 820, a determination is made whether the sensor data from each sensor is within a predetermined set of parameters. After the sensor data has been processed, the process 627 then moves to a step 825, wherein the state of the injection device is determined. The determination can be performed by a microprocessor, such as microprocessor 150 depicted in FIG. 2A. In an illustrative embodiment, the state of the device can include, but is not limited to, ready-to-use, not-ready, fault, refrigerated, warming up, inside packaging, or outside of packaging.

After the state of the device is determined, the process 627 moves to a step 830, wherein indicator parameters are updated. In the step 830, there is a determination of what will be displayed by one or more status indicators of the module. The process 627 then concludes with an end step.

Figure 9:
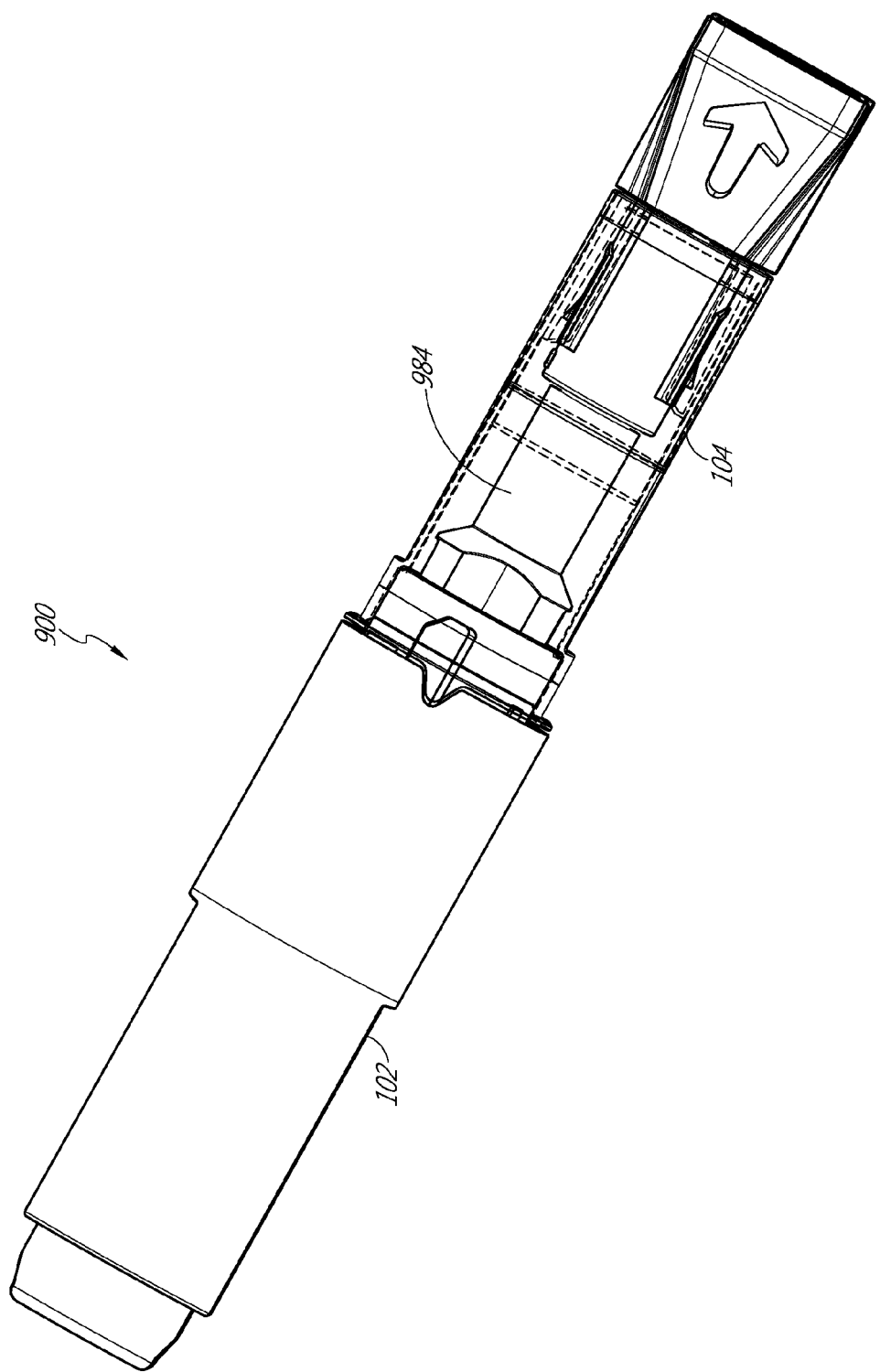
FIG. 9 depicts an injection device with a module in accordance with an illustrative embodiment of the present invention.

FIG. 9 depicts an illustrative embodiment of an injection device 900. The injection device 900 comprises the same or generally similar features as those described with respect to the injection device 100. The injection device 900 further includes a needle shield 984. The needle shield 984 is positioned within an interior volume of the lower portion 104 of the injection device 900. The needle shield 984 is configured to extend beyond the tip of an autoinjector needle to at least partially conceal the autoinjector needle when the injection device 900 is not in use. The needle shield 984 is further configured to retract within the interior volume of the injection device 900 towards the upper portion 102 when a force is applied to the end of the needle shield 984 extending beyond the autoinjector needle, such as, for example, when a user contacts the needle shield 984 to a surface of skin and pushes the injection device towards the surface of the skin. When the needle shield 984 retracts, the autoinjector needle may be exposed, allowing the needle to pierce the surface of the skin.

In operation, injection device 900 can perform essentially the same functions as injection device 100. A module located in the interior volume of the injection device 900 is configured to monitor and detect events and characteristics associated with the use of an injection device. Sensing can be performed by contact and/or non-contact methods, including but not limited to microswitch sensing, electrostatic sensing, capacitive sensing, optical sensing, infrared (IR) sensing, and magnetic sensing. The module can then communicate various conditions and states of the injection device to a user through visual, auditory, or tactile stimuli or can transmit that data to an external device. Visual and/or auditory stimuli can be communicated using the status indicators mounted on the module.

Figure 10:
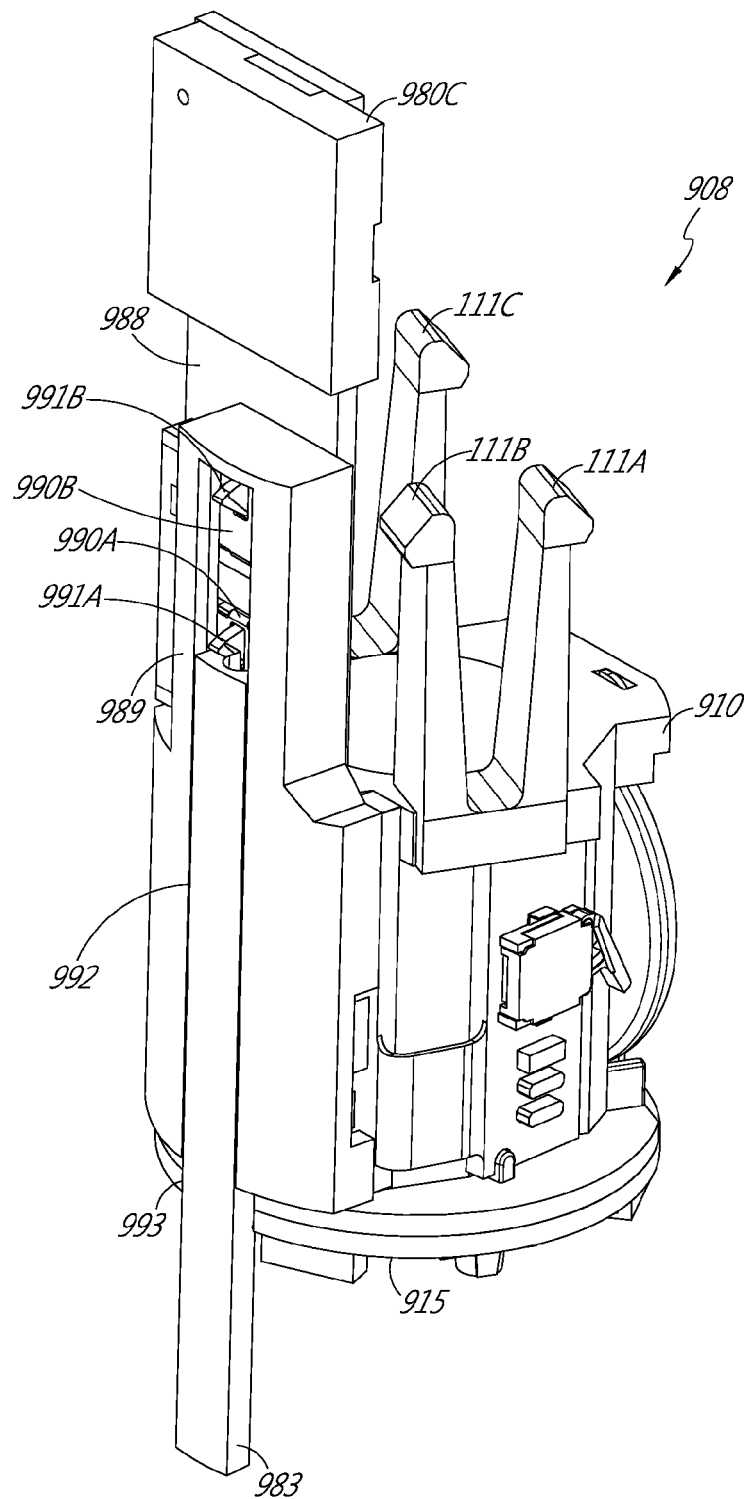
FIG. 10 depicts a module in accordance with an illustrative embodiment of the present invention.

FIG. 10 depicts an illustrative embodiment of a module 908 according to the present invention. The module 908 is configured to fit within the interior of an injection device such as injection device 900 and comprises the same or generally similar features as those described with respect to module 108. Module 908 comprises a carrier 910. The carrier 910 comprises generally similar features as described with respect to the carrier 110. The carrier 910 is cylindrical in shape and has openings for the separate parts of the module 908.

One side of the carrier 910 comprises a surface 988. The surface 988 extends along the length of the module 908 and beyond a distal end of the upper tangs 111A,B,C,D, protruding into the interior volume of the upper portion 104 of the injection device 900.

A status indicator 980C is mounted to the surface 988 at a section of the surface 988 extending furthest into the interior volume of the upper portion 102 of the injection device 900. The status indicator 980C comprises a speaker configured to produce auditory stimuli to notify a user of a condition or state of the device, either alone or in combination with other status indicators. Different auditory stimuli can indicate different conditions or states of the injection device 900. Examples of conditions or states of the device include, but are not limited to, ready-to-use, not-ready, fault, refrigerated, warming up, inside packaging, outside of packaging, needle shield retracted, or needle shield not retracted. Each auditory stimulus can include one or more tones. Multiple tones may be used in combination or in series. Tones for each auditory stimulus may also vary in pitch, volume, and duration. In some embodiments, an auditory stimulus can include a voice recording reciting one or more conditions or states of the injection device 900. In some embodiments, the status indicator 980C comprises an SMD piezoelectric sounder The electronics package 125 (not shown), a pair of electronic switches 991A and 991B, and a cover 989 are also mounted to the surface 988. The cover 989 at least partially encloses the exterior surface of the electronics package 125. The cover 989 further comprises a channel 992. Positioned near a first end of the channel 992 are openings 990A,B. The electronic switches 991A and 991B protrude from the openings 990A,B.

The channel 992 of the cover 989 is further configured to receive a shield contact 983. The shield contact 983 is configured to move along the channel 992. The shield contact 983 further extends from a second end of the channel 992 through a channel 993 of a top surface 915 of the module 908 and into the interior volume of the lower portion 104 of the injection device 900. The channel 993 is further configured to allow for movement of the shield contact 983 therein.

Figure 11:
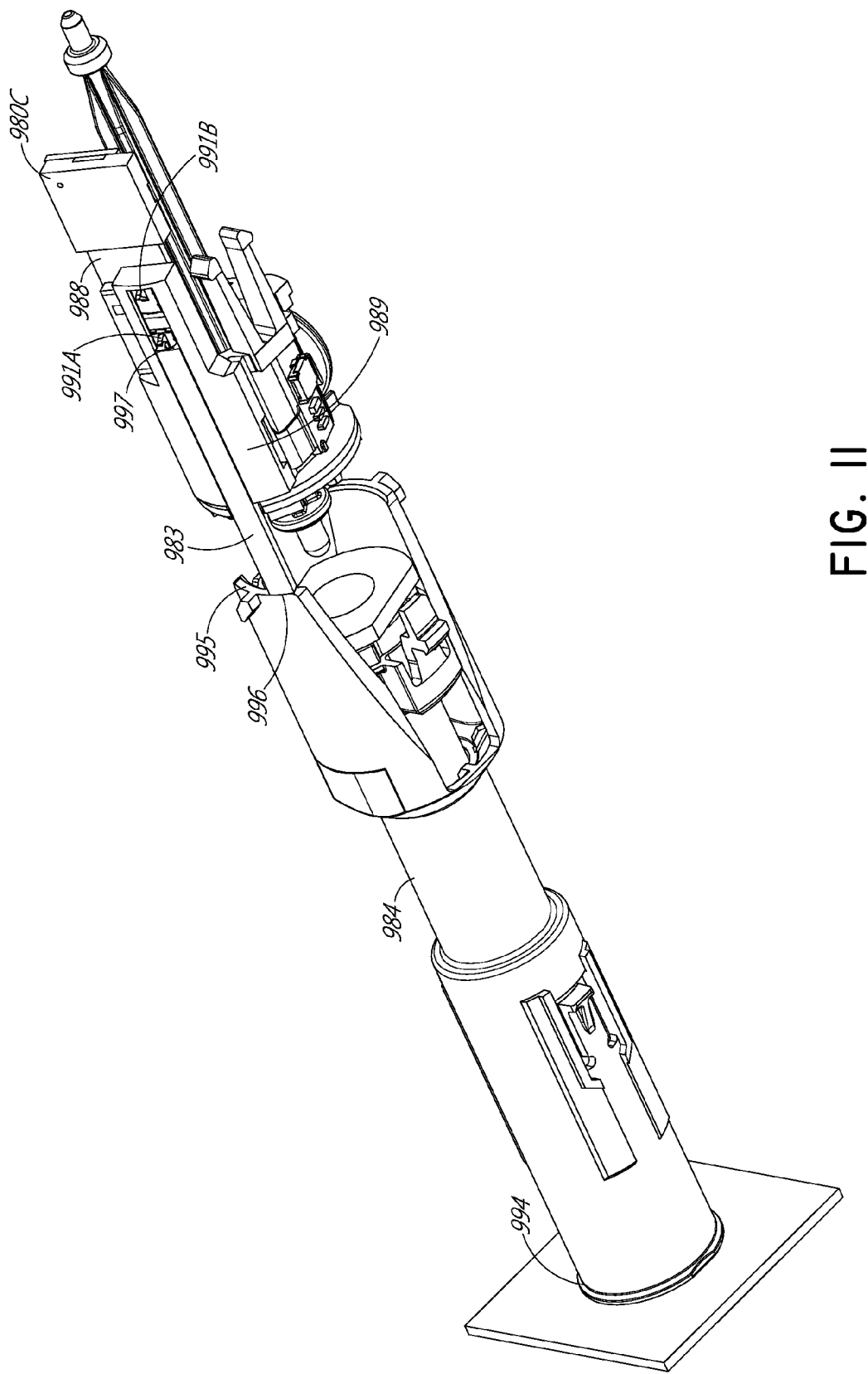
FIG. 11 depicts a sectional view showing several interior components of an injection device with a module in accordance with an illustrative embodiment of the present invention.

FIG. 11 depicts a sectional view showing several interior components of the injection device 900 including the needle shield 984 and the module 908 in accordance with an illustrative embodiment of the present invention. A distal surface 994 of the needle shield can extend beyond a tip of a needle of the injection device 900. The needle shield 984 can be configured such that upon the application of force to the distal surface 994 in a direction towards the upper portion 102 of the injection device 900, the needle shield 984 retracts toward the upper portion 102 of the injection device 900, exposing the tip of the needle.

An upper surface 995 of the needle shield 984 engages a first end 996 of the shield contact 983. Retraction of the needle shield 984 towards the upper portion 102 of the injection device 900 can cause movement of the shield contact 983 within the channel 992 towards the upper portion 102 of the injection device 900. As the shield contact 983 moves within the channel 992, a second end 997 of the shield contact 983 can engage the electronic switches 991A,B. Accordingly, engagement of the electronic switches 991A,B can indicate the location of the needle shield 984 in reference to needle.

The electronic switches 991A,B may be in communication with microprocessor 150. The microprocessor 150 may be configured to determine a state or condition of the device based at least in part on data received from the electronic switches 991A,B, such as, for example, needle shield retracted, or needle shield not retracted. Data received from the electronic switches 991A,B may comprise sensor data, as described above with reference to FIGS. 2A-8. If the needle shield is retracted, this may indicate to a user that the needle is piercing the surface of the skin. If the needle shield is not retracted, this may indicate to a user that the needle shield is not piercing the skin.

Figure 12:
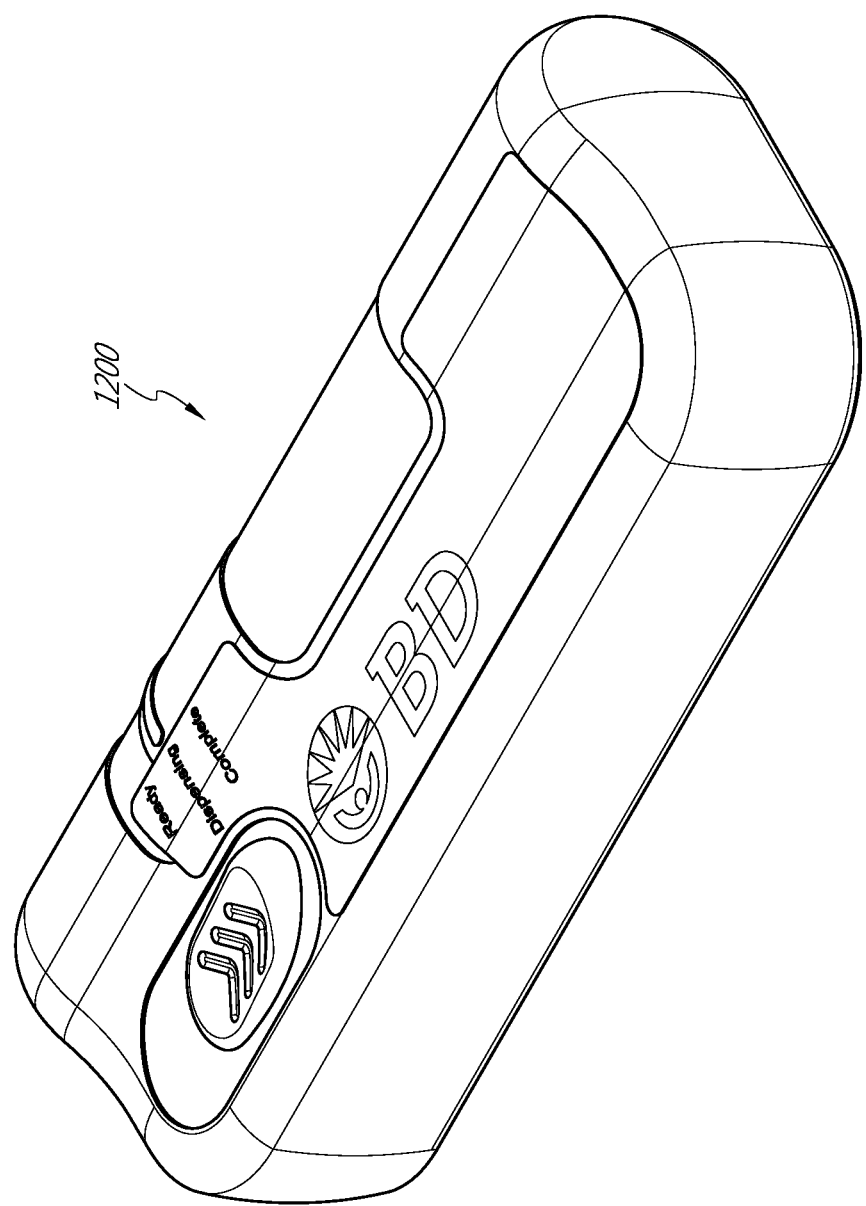
FIG. 12 depicts an injection device with a module in accordance with an illustrative embodiment of the present invention.

FIG. 12 depicts an illustrative embodiment of an injection device 1200. The injection device 1200 comprises a patch injector, such as a LIBERTAS™ patch injector from Becton Dickinson®. The injection device 1200 is configured to adhere to the skin to allow for hands-free medicament delivery. The injection device 1200 is also configured to allow for medicament delivery over extended periods of time. In some embodiments, delivery may range from a few seconds to a several minutes. Medicament delivery may be performed through a needle and/or catheter housed within the interior of the injection device 1200. The injection device 1200 may be disposable. Alternatively, the injection device 1200 may be configured for repeated use.

In some embodiments, upon activation of the injection device 1200, a needle extends from an opening of the injection device into a surface of a user's skin. After a period of time, a catheter may extend from the same opening and at least partially enclose the needle. The needle may then retract into the interior surface of the injection device 1200. Medicament may be delivered through the catheter.

In operation, injection device 1200 can perform essentially the same functions as injection device 100 of the injection device 900. A module located in the interior volume of the injection device 1200 is configured to monitor and detect events and characteristics associated with the use of an injection device. Sensing can be performed by contact and/or non-contact methods, including but not limited to microswitch sensing, electrostatic sensing, capacitive sensing, optical sensing, infrared (IR) sensing, and magnetic sensing. The module can then communicate various conditions and states of the injection device to a user through visual, auditory, or tactile stimuli or can transmit that data to an external device. Visual and/or auditory stimuli can be communicated using the status indicators mounted on the module.

Figure 13:
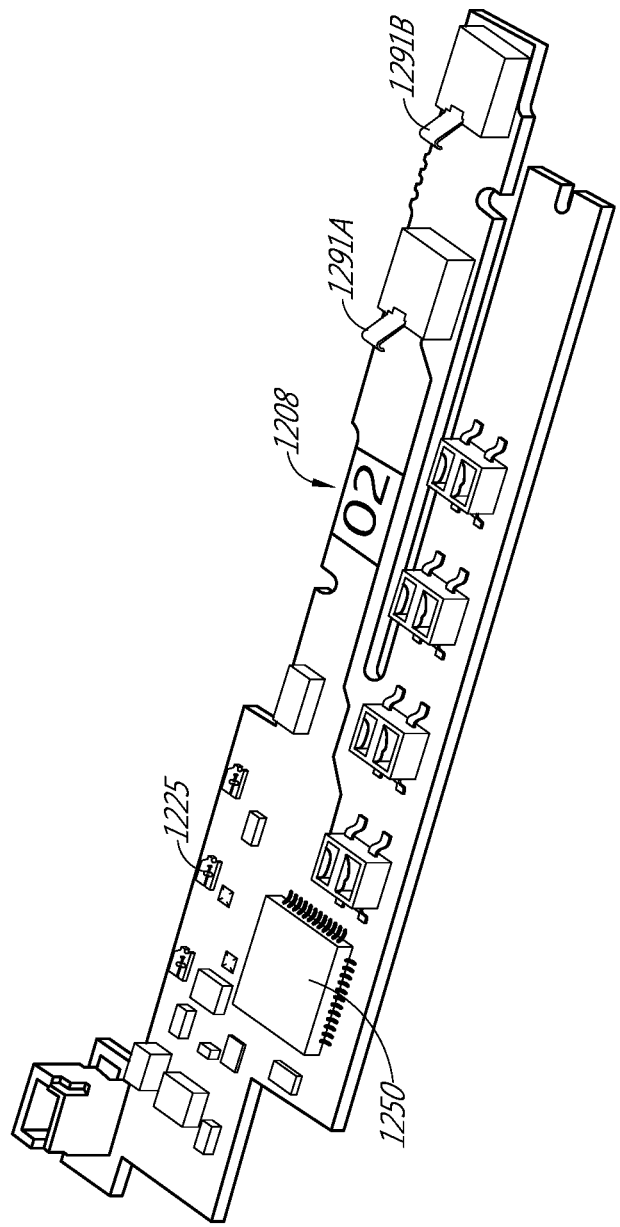
FIG. 13 depicts a module in accordance with an illustrative embodiment of the present invention.

FIG. 13 depicts a module 1208 in accordance with an illustrative embodiment of the present invention. The module 1208 is configured to fit within the interior volume of the injection device 1200. The module 1208 can comprise the same or generally similar features as the modules 108 and 908, such as, for example, a battery, an electronics package 1225, a computing module 1250, a communication module, one or more sensors, a plurality of electrical switches 1291A,B, and one or more status indicators. In operation, the module 1208 can perform essentially the same functions as the module 108 or the module 908.

Figure 14:
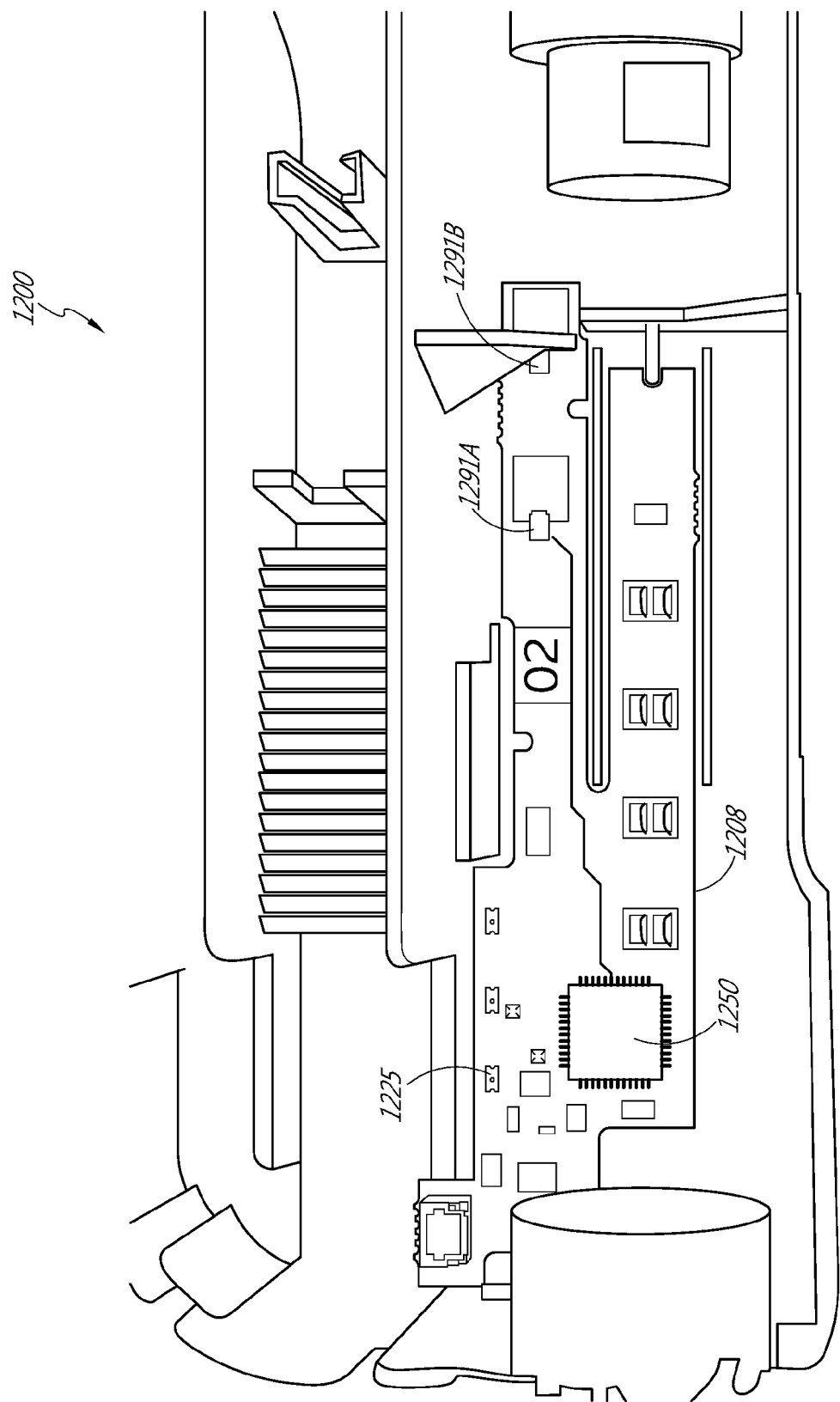
FIG. 14 depicts a sectional view showing several interior components of an injection device with a module in accordance with an illustrative embodiment of the present invention.

FIG. 14 depicts a sectional view of the injection device 1200 showing the module 1208 secured within the interior volume of the injection device 1200 in accordance with an illustrative embodiment of the present invention.

Figure 15:
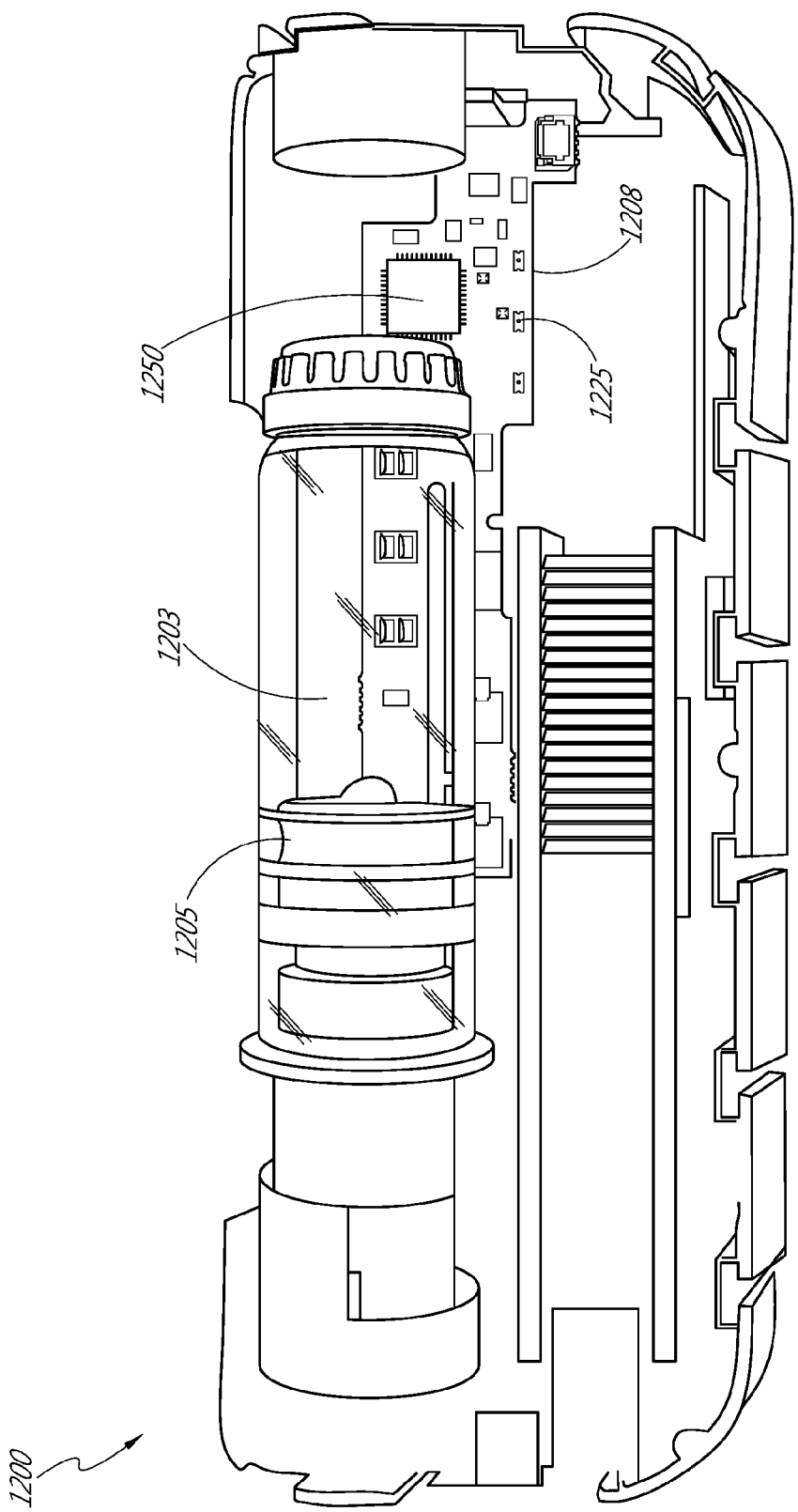
FIG. 15 depicts a sectional view showing several interior components of an injection device with a module in accordance with an illustrative embodiment of the present invention.

FIG. 15 shows a sectional view of the injection device 1200 showing the interior volume of the injection device 1200 with the module 1208 and a medicament vial 1203. The medicament vial 1203 is configured to store medicament prior to injection into a user. The medicament vial 1203 includes a plunger 1205. Movement of the plunger within the medicament vial 1203 can cause medicament to flow from the medicament vial 1203 and out of the medicament delivery device 1200. Electrical switches 1291A,B can be configured to interact with the plunger 1205 so that movement of the plunger 1205 can cause the activation of the electrical switches 1291A,B. In some embodiments, the module 1208 comprises sensors for collecting parameter data related to the medicament stored in the medicament vail 1203, including but not limited to temperature, light, motion, orientation, amount of medicament present, rate of medicament delivery, and end of dose.

Implementations disclosed herein provide systems, methods and apparatus for a module configured to mate with an injector device. One skilled in the art will recognize that these embodiments may be implemented in hardware, software, firmware, or any combination thereof.

The functions described herein may be stored as one or more instructions on a processor-readable or computer-readable medium. The term "computer-readable medium" refers to any available medium that can be accessed by a computer or processor. By way of example, and not limitation, such a medium may comprise RAM, ROM, EEPROM, flash memory, CD-ROM or other optical disk storage, magnetic disk storage or other magnetic storage devices, or any other medium that can be used to store desired program code in the form of instructions or data structures and that can be accessed by a computer. Disk and disc, as used herein, includes compact disc (CD), laser disc, optical disc, digital versatile disc (DVD), floppy disk and Blu-ray® disc where disks usually reproduce data magnetically, while discs reproduce data optically with lasers. It should be noted that a computer-readable medium may be tangible and non-transitory. The term "computer-program product" refers to a computing device or processor in combination with code or instructions (e.g., a "program") that may be executed, processed or computed by the computing device or processor. As used herein, the term "code" may refer to software, instructions, code or data that is/are executable by a computing device or processor.

Software or instructions may also be transmitted over a transmission medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of transmission medium.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component or directly connected to the second component. As used herein, the term "plurality" denotes two or more. For example, a plurality of components indicates two or more components.

The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

In the foregoing description, specific details are given to provide a thorough understanding of the examples. However, it will be understood by one of ordinary skill in the art that the examples may be practiced without these specific details. For example, electrical components/devices may be shown in block diagrams in order not to obscure the examples in unnecessary detail. In other instances, such components, other structures and techniques may be shown in detail to further explain the examples.

Headings are included herein for reference and to aid in locating various sections. These headings are not intended to limit the scope of the concepts described with respect thereto. Such concepts may have applicability throughout the entire specification.

It is also noted that the examples may be described as a process, which is depicted as a flowchart, a flow diagram, a finite state diagram, a structure diagram, or a block diagram. Although a flowchart may describe the operations as a sequential process, many of the operations can be performed in parallel, or concurrently, and the process can be repeated. In addition, the order of the operations may be re-arranged. A process is terminated when its operations are completed. A process may correspond to a method, a function, a procedure, a subroutine, a subprogram, etc. When a process corresponds to a software function, its termination corresponds to a return of the function to the calling function or the main function.

The previous description of the disclosed implementations is provided to enable any person skilled in the art to make or use the present invention. Various modifications to these implementations will be readily apparent to those skilled in the art, and the generic principles defined herein may be applied to other implementations without departing from the spirit or scope of the invention. Thus, the present invention is not intended to be limited to the implementations shown herein but is to be accorded the widest scope consistent with the principles and novel features disclosed herein.

What is claimed is:

1. A module for detecting environmental parameters, comprising:
    a carrier configured to mate with an injection device;
    one or more environmental sensors mounted on the carrier;
    at least one indicator; and
    a processor configured to read parameters from the environmental sensors and activate the indicator if a predetermined event occurs;
    wherein the module is configured to fit within the interior of the injection device.

2. The module of claim 1, wherein the injection device is an autoinjector.

3. The module of claim 1, wherein the presence of the module does not affect a pre-existing function of the injection device.

4. The module of claim 1, wherein the injection device is a single dose medicament injection device and the processor is configured to activate the indicator when the environmental parameters are outside of the safe storage parameters for a drug.

5. The module of claim 1, wherein the carrier comprises an electronic switch configured to activate in response to an input that initiates an injection event.

6. The module of claim 1, wherein the environmental sensors are selected from the group consisting of: sensors for temperature, pressure, motion, orientation, and electromagnetic radiation.

7. The module of claim 1, wherein the at least one indicator comprises an indicator selected from the group consisting of visible, audible, and haptic indicators.

8. The module of claim 1, wherein the injection device is a patch injector.

9. The module of claim 1, further comprising a transmitter configured to transmit one or more of activation data and environmental sensor data to an external device.

10. A method of detecting activation of an injection device, comprising:
    providing an injection device configured to administer a medicament;
    providing a module comprising a processor, wherein the module attaches to the injection device and is configured to fit within the interior of the injection device, wherein the module is configured to detect environmental parameters using one or more sensors communicating with the processor; and
    activating an indicator on the module if a predetermined event is detected.

11. The method of claim 10, wherein the injection device is an autoinjector.

12. The method of claim 10, wherein the presence of the module does not affect a pre-existing function of the injection device.

13. The method of claim 10, wherein the injection device is a single dose medicament injection device and the processor is configured to activate the indicator when the environmental parameters are outside of the safe storage parameters for a drug.

14. The method of claim 10, wherein the module carrier comprises an electronic switch configured to activate in response to an input that initiates an injection event.

15. The method of claim 10, wherein the environmental sensors are selected from the group consisting of: sensors for temperature, pressure, motion, orientation, and electromagnetic radiation.

16. The method of claim 10, wherein the at least one indicator comprises an indicator selected from the group consisting of visible, audible, and haptic indicators.

17. The method of claim 10, wherein the injection device is a patch injector.

18. The method of claim 10, further comprising transmitting one or more of activation data and environmental sensor data to an external device.

19. A module for detecting environmental parameters, comprising:
- a carrier configured to mate with an injection device, wherein the carrier comprises an electronic switch configured to activate in response to an input that initiates an injection event;
- one or more environmental sensors mounted on the carrier;
- at least one indicator; and
- a processor configured to read parameters from the environmental sensors and activate the indicator if a predetermined event occurs.

20. The module of claim 19, wherein the environmental sensors are selected from the group consisting of: sensors for temperature, pressure, motion, orientation, and electromagnetic radiation.

21. The module of claim 19, wherein the at least one indicator comprises an indicator selected from the group consisting of visible, audible, and haptic indicators.

22. The module of claim 19, further comprising a transmitter configured to transmit one or more of activation data and environmental sensor data to an external device.

* * * * *